(12) United States Patent
Wu et al.

(10) Patent No.: US 10,098,853 B2
(45) Date of Patent: Oct. 16, 2018

(54) COMPOSITION FOR TREATING ATHEROSCLEROSIS AND A PREPARATION METHOD THEREOF

(71) Applicant: KAOHSIUNG MEDICAL UNIVERSITY, Kaohsiung (TW)

(72) Inventors: Yang-Chang Wu, Kaohsiung (TW); Fang-Rong Chang, Kaohsiung (TW); Tusty-Jiuan Hsieh, Kaohsiung (TW); Suh-Hang Juo, Kaohsiung (TW); An-Shen Lin, Taipei (TW); Ying-Chi Du, Chiayi (TW)

(73) Assignee: Kaohsiung Medical University, Kaosiung (TW)

( * ) Notice: Subject to any disclaimer, the term of this patent is extended or adjusted under 35 U.S.C. 154(b) by 124 days.

(21) Appl. No.: 14/202,564

(22) Filed: Mar. 10, 2014

(65) Prior Publication Data

US 2014/0194474 A1  Jul. 10, 2014

Related U.S. Application Data

(62) Division of application No. 13/570,963, filed on Aug. 9, 2012.

(30) Foreign Application Priority Data

Aug. 10, 2011  (TW) .............................. 100128614 A

(51) Int. Cl.
*C07C 49/84* (2006.01)
*A61K 31/12* (2006.01)
(Continued)

(52) U.S. Cl.
CPC ............ *A61K 31/12* (2013.01); *A61K 31/122* (2013.01); *A61K 31/352* (2013.01);
(Continued)

(58) Field of Classification Search
CPC .... A61K 31/12; A61K 31/352; A61K 31/122; A61K 45/06; A61K 31/4439; C07C 49/84; C07C 49/835
See application file for complete search history.

(56) References Cited

U.S. PATENT DOCUMENTS

| 4,867,964 A | 9/1989 | Forestier et al. |
| 7,572,831 B2 | 8/2009 | Kim et al. |

(Continued)

FOREIGN PATENT DOCUMENTS

WO  WO2009/026658  *  3/2009  .......... C07D 231/10

OTHER PUBLICATIONS

Siegel et al CA Cancer J Clin 2012;62:220-241.*

(Continued)

*Primary Examiner* — Angela C Brown-Pettigrew
(74) *Attorney, Agent, or Firm* — Volpe and Koenig, P.C.

(57) ABSTRACT

Disclosed are a composition for preventing and treating atherosclerosis which includes chalcone compound. In particular, the chalcone compound bound with 2-hydroxyl in ring A and 4'-methyoxy in ring B has versatile therapeutic potentials on anti-atherosclerosis by acting as PPARγ inducer, p44/42 MAPK inhibitor and cell cycle blocker and does not show toxicity to human aortic smooth muscle cells (HASMCs). In addition, the chalcone compound exhibits synergistic effect with the PPARγ ligand (rosiglitazone) to inhibit cell proliferation and the upregulation of cyclin D1, cyclin D3, interleukin-1β (IL-1β) and interleukin-6 (IL-6) induced by oxidized low density lipoprotein (Ox-LDL).

7 Claims, 10 Drawing Sheets

Specification includes a Sequence Listing.

(51) Int. Cl.
*A61K 31/4439* (2006.01)
*C07C 49/835* (2006.01)
*A61K 45/06* (2006.01)
*A61K 31/122* (2006.01)
*A61K 31/352* (2006.01)

(52) U.S. Cl.
CPC .......... *A61K 31/4439* (2013.01); *A61K 45/06* (2013.01); *C07C 49/835* (2013.01); *C07C 49/84* (2013.01)

(56) References Cited

U.S. PATENT DOCUMENTS

2009/0124688 A1* 5/2009 Lin ..................... A61K 31/353
 514/530
2013/0040996 A1 2/2013 Wu et al.

OTHER PUBLICATIONS

Sowers et al Hypertension. 2001;37:1053-1059.*
Ridker, Circulation. 2002;105:2-4.*
Patani et al, (Bioisosterism: Rational approach in drug design, Chem. Rev., 1996, 3147-3176) (Year: 1996).*
Ahmad Aljada, Laura O'Connor, Yu-Yen Fu and Shaker A. Mousa, "PPARγ ligands, rosiglitazone and pioglitazone, inhibit bFGF- and VEGF-mediated angiogenesis", Angiogenesis, vol. 11, pp. 361-367 (2008).
J. Mojzisa, L. Varinskaa, G. Mojzisovab, I. Kostovac and L. Mirossaya, "Antiangiogenic effects of flavonoids and chalcones", Pharmacological Research, vol. 57, pp. 259-265 (2008).
Jun Liu, Babak Razani, Shaoqing Tang, Bruce I. Terman, J. Anthony Ware and Michael P. Lisanti, "Angiogenesis Activators and inhibitors Differentially Regulate Caveolin-1 Expression and Caveolae Formation in Vascular Endothelial Cells", The Journal of Biological Chemistry, vol. 274, pp. 15781-15785 (1999).

* cited by examiner

SEQUENCE LISTING

<160> NUMBER OF SEQ ID NOS: 10

<210> SEQ ID NO 1
<211> LENGTH: 23
<212> TYPE: DNA
<213> ORGANISM: Homo sapiens
<300> PUBLICATION INFORMATION:
<308> DATABASE ACCESSION NUMBER: NM_00576
<309> DATABASE ENTRY DATE: 2011-05-01
<313> RELEVANT RESIDUES IN SEQ ID NO: (164)..(186)

<400> SEQUENCE: 1
ctgatggccc taaacagatg aag                                           23

<210> SEQ ID NO 2
<211> LENGTH: 17
<212> TYPE: DNA
<213> ORGANISM: Homo sapiens
<300> PUBLICATION INFORMATION:
<308> DATABASE ACCESSION NUMBER: NM_000576
<309> DATABASE ENTRY DATE: 2011-05-01
<313> RELEVANT RESIDUES IN SEQ ID NO: (234)..(250)

<400> SEQUENCE: 2
ggtcggagat tcgtagc                                                  17

<210> SEQ ID NO 3
<211> LENGTH: 18
<212> TYPE: DNA
<213> ORGANISM: Homo sapiens
<300> PUBLICATION INFORMATION:
<308> DATABASE ACCESSION NUMBER: NM_000600
<309> DATABASE ENTRY DATE: 2011-05-22
<313> RELEVANT RESIDUES IN SEQ ID NO: (178)..(195)

<400> SEQUENCE: 3
tgttgcctgc tgccttcc                                                 18

<210> SEQ ID NO 4
<211> LENGTH: 20
<212> TYPE: DNA
<213> ORGANISM: Homo sapiens
<300> PUBLICATION INFORMATION:
<308> DATABASE ACCESSION NUMBER: NM_000600
<309> DATABASE ENTRY DATE: 2011-05-22
<313> RELEVANT RESIDUES IN SEQ ID NO: (349)..(368)

<400> SEQUENCE: 4
tgcctctttg ctgctttcac                                               20

<210> SEQ ID NO 5
<211> LENGTH: 20
<212> TYPE: DNA
<213> ORGANISM: Homo sapiens
<300> PUBLICATION INFORMATION:
<308> DATABASE ACCESSION NUMBER: NM_005036
<309> DATABASE ENTRY DATE: 2011-05-15
<313> RELEVANT RESIDUES IN SEQ ID NO: (1057)..(1076)

<400> SEQUENCE: 5
agaacaagga ggcggaggtc                                               20

<210> SEQ ID NO 6
<211> LENGTH: 21
<212> TYPE: DNA
<213> ORGANISM: Homo sapiens
<300> PUBLICATION INFORMATION:
<308> DATABASE ACCESSION NUMBER: NM_005036

```
<309> DATABASE ENTRY DATE: 2011-05-15
<313> RELEVANT RESIDUES IN SEQ ID NO: (1153)..(1173)

<400> SEQUENCE: 6
tcaggtccaa gtttgcgaag c                                                   21

<210> SEQ ID NO 7
<211> LENGTH: 24
<212> TYPE: DNA
<213> ORGANISM: Homo sapiens
<300> PUBLICATION INFORMATION:
<308> DATABASE ACCESSION NUMBER: NM_138711
<309> DATABASE ENTRY DATE: 2011-05-22
<313> RELEVANT RESIDUES IN SEQ ID NO: (1404)..(1427)

<400> SEQUENCE: 7
tggaattaga tgacagcgac ttgg                                                24

<210> SEQ ID NO 8
<211> LENGTH: 20
<212> TYPE: DNA
<213> ORGANISM: Homo sapiens
<300> PUBLICATION INFORMATION:
<308> DATABASE ACCESSION NUMBER: NM_138711
<309> DATABASE ENTRY DATE: 2011-05-22
<313> RELEVANT RESIDUES IN SEQ ID NO: (1540)..(1559)

<400> SEQUENCE: 8
aggactcagg gtggttcagc                                                     20

<210> SEQ ID NO 9
<211> LENGTH: 21
<212> TYPE: DNA
<213> ORGANISM: Homo sapiens
<300> PUBLICATION INFORMATION:
<308> DATABASE ACCESSION NUMBER: NM_001101
<309> DATABASE ENTRY DATE: 2011-05-21
<313> RELEVANT RESIDUES IN SEQ ID NO: (697)..(717)

<400> SEQUENCE: 9
gagcgggaaa tcgtgcgtga c                                                   21

<210> SEQ ID NO 10
<211> LENGTH: 23
<212> TYPE: DNA
<213> ORGANISM: Homo sapiens
<300> PUBLICATION INFORMATION:
<308> DATABASE ACCESSION NUMBER: NM_001101
<309> DATABASE ENTRY DATE: 2011-05-21
<313> RELEVANT RESIDUES IN SEQ ID NO: (862)..(884)

<400> SEQUENCE: 10
aggaaggaag gctggaagag tgc                                                 23
```

COMPOSITION FOR TREATING ATHEROSCLEROSIS AND A PREPARATION METHOD THEREOF

CROSS-REFERENCE TO RELATED APPLICATIONS AND CLAIM OF PRIORITY

This application is a divisional application of U.S. patent application Ser. No. 13/570,963 filed Aug. 9, 2012, which claims the benefit of Taiwan Patent Application No. 100128614, filed on Aug. 10, 2011, in the Taiwan Intellectual Property Office, the disclosures of which are incorporated herein in their entirety by reference.

FIELD OF THE INVENTION

The present invention relates to a chalcone composition and the preparation method thereof. In particular, the present invention relates to a composition for preventing and treating atherosclerosis and the preparation method thereof.

BACKGROUND OF THE INVENTION

Cardiovascular disease is a symptom of heart and blood vessels. Cardiovascular disease can be grouped as coronary artery heart disease, cerebrovascular disease, peripheral arterial occlusion disease, rheumatic heart disease, congenital heart disease, deep vein thrombosis and pulmonary embolism. Ischemic heart disease, myocardial infarction or sudden death will be induced if coronary arteriosclerosis occurs. The occurrence of cerebral or carotid arteriosclerosis will result in renal hypertension and even uremia. Peripheral arteriosclerosis will result in aneurism or atherosclerosis obliterans. Therefore, arteriosclerosis is closely associated with cardiovascular diseases.

The causes of atherosclerosis are hyperlipidemia or hemagglutination. For instance, lipopolysaccharide (LPS) activates cytokines, tumor necrosis factor-alpha (TNF-α) and interleukin-6 (IL-6), and further stimulates the proliferation of smooth muscle cells and increases the generation of adhesion factors. In addition, LPS will interact with toll-like receptor (TLR4) region on endothelial cells or macrophages, and then activates nuclear factor-kappa B (NF-κB) and p44/p42 mitogen-activated protein kinase (MAPK) pathways. Accordingly, inflammation induced by LPS will result in arteriosclerosis.

Atherosclerosis belongs to an inflammation, and the damaged vascular endothelial cells will result in hindrance of vascular endothecium and changes of permeability. Abundant low density lipoprotein (LDL) enters into endothelial cells, and oxidized-LDL (Ox-LDL) is reproduced to stimulate endothelial cells or smooth muscle cells to generate chemotaxis materials, which attract monocytes entering into the lower space of endothelial cells, and monocytes are transformed as macrophages which engulf Ox-LDL to form foam cells. The accumulation of a plenty of foam cells enhances cytokines, growth factors and prostagladin. Cytokines stimulates the proliferation of smooth muscle cells in the mesoderm of vessels, and smooth muscle cells are moved to endoderm to divide/proliferate and reproduce collagenous fibers to form plaques, attract the adhesion and aggregation of platelets, and form thrombus to block the blood flow, so that the acute diseases such as the unstable angina cordis, the acute myocardial infarction and stroke etc. occur in clinics.

Currently, the drugs for treating atherosclerosis usually are antilipemic agents or antithrombotic agents.

The antilipemic agents are divided as four groups, bile acid sequestrant resin, fibric acid derivative, nicotinic acid derivative and statin drug. (1) The bile acid sequestrant resin blocks bile acid in the gastrointestinal tract from absorption, increases the compensation of liver to reproduce bile acid using cholesterol and reduces the amount of cholesterol in the liver cells. However, the side effect of stomach upset (diarrhea or constipation) might occur. (2) The fibric acid derivative decreases the concentration of triglyceride in the blood, and it might induce the side effects such as gripes, diarrhea, nausea, vomit, the upgrade of liver function indexes and so on. (3) Nicotinic acid derivative is capable of reducing the concentrations of LDL, triglyceride and cholesterol, and is capable of increasing the concentration of high density lipoprotein (HDL). Nevertheless, the side effects such as stomach upset, hyperuricacidemia, gout, exanthema and the upgrade of liver function indexes and so on would occur. The probability of gallstones might be increased due to a long term administration. (4) Statin drug is the most effective and the most common antilipemic agent, which inhibits the rate-limited enzyme for cholesterol synthesis in liver cells and further reduces the amount of cholesterol in the blood. The side effects includes the upgrade of liver function indexes, headache, gripes and weariness, etc.

Antithrombotic agents are divided as three groups, anticoagulant, antiplatelet drug and thrombolytic agent. Anticoagulant further is divided as four sub-groups, vitamin K antagonist, heparin and its derivative, direct thrombin inhibitor and other anticoagulant drugs. (1) Vitamin K antagonist includes Warfarin (also is a pesticide against rats and mice), dicoumarin and so on. Its chemical structure is similar to that of vitamin K, and its functional mechanism is to counteract the activity responses of vitamin K-dependent coagulation factors II, VII, IV and X. However, Vitamin K antagonist will result in the side effects such as hematuria, gastrointestinal bleeding, intracerebral hemorrhage and so on. (2) Heparin is composed of D-glucamine interacting with L-iduronic acid and D-glucuronic acid. Heparin is conjugated with the anti-coagulation factor III first, and then accelerates thrombin inactivation to achieve anti-coagulation. Heparin also can be conjugated with a plenty of coagulation factors such as IIa, Xa, XIa and XIIa, to inactivate coagulation factors. However, heparin might generate the side effects such as bleeding, hypersensitivity, platelet deficiency disease and so on. (3) Direct thrombin inhibitor includes hirudin and bivalirudin, etc., wherein hirudin is a 65-amino acid protein which is obtained from the salivary gland of leech and plays the critical role in hemostasis and inhibition of thrombus formation. Although hirudin is the most effective natural anticoagulant, it is difficult to extract it from leeches and hirudin must be prepared with the recombinant biotechnology. (4) The examples of other anticoagulant drug includes ramatroban which is a thromboxane receptor inhibitor.

Antiplatelet drug further is divided as five sub-groups, COX inhibitor, adenosine diphosphate (ADP) receptor inhibitor, phosphodiesterase (PDE) inhibitor, adenosine reuptake inhibitor and thromboxane inhibitor.

Among COX inhibitors, aspirin (low dosage) can inhibit platelet aggregation and prevent thrombosis formation. Since aspirin will reduce the secretion of protection materials in stomach, so that side effects, e.g. stomach upset, gastrointestinal bleeding and so on, would occur. Among ADP receptor inhibitors, Clopidogrel would have the risk of stomach bleeding. Among PDE inhibitors, Cilostazol could inhibit phosphodiesterase (PDE) activity (especially selectively to PDE III) and impede the cyclic adenosine monophosphate (cAMP) metabolism in cells, and promote the increase of cAMP concentration in platelets and vessels. Thus, Cilostazol has the functions of anti-platelet aggregation and angiectasis, but results in side effects such as headache, diarrhea, vomit, erythematous rash, and hematological abnormality, etc. Among adenosine reuptake inhibitors, dipyridamole could inhibit platelet aggregation caused by platelet activation factors, collagen, ADP and so on, and it side effects are vertigo, dizziness, fainting, flame, headache, vomit, emesis, exanthema on skin, gripes and weakness, etc. When dipyridamole is administered with heparin, bleeding risk would be increased. Among thromboxane inhibitors, Terutroban can block platelet aggregation and vasoconstriction induced by thromboxane, promote endoderm's functions and has anti-atherosclerosis effect, whereas it also has the bleeding risk.

The efficacies of thrombolytic agent lie in activating plasmin and promoting fibriolysis. Thrombolytic agent is suitable for treating deep vein thrombosis, pulmonary embolism, acute myocardial infarction and acute arterial embolism, but it will result in bleeding and hypersensitivity.

Since the aforementioned two classes of atherosclerosis therapeutic drugs have different chemical structures and will generate plural side effects, developing new drugs in treatment of atherosclerosis and avoiding the generation of side effects become the important issues.

It is therefore attempted by the applicant to deal with the above situation encountered in the prior art.

SUMMARY OF THE INVENTION

Multiple chalcone compounds are synthesized in the present invention, and they have various inhibition effects on the cell proliferation of human aortic smooth muscle cells (HASMCs) stimulated by LPS. In addition, when the chalcone compound 1 has ortho-hydroxy (2-OH) in ring A and para-methoxy (4'-OCH$_3$) in ring B, compound 1 has the best activity on inhibiting HASMCs proliferation induced by Ox-LDL, is non-toxic to cells and is capable of inhibiting inflammation, as compared with other flavonoid compounds. Compound 1 shows synergism with the ligand (e.g. the commercialized rosiglitazone) of peroxisome proliferator activated receptor gamma (PPARγ), to inhibit the cell proliferation induced by Ox-LDL, cyclin D1 and D3 expression and interleukin-1β (IL-1β) and interleukin 6 (IL-6) expression.

Therefore, the present invention provides a composition for preventing and/or treating atherosclerosis, including a chalcone compound represented by Formula I:

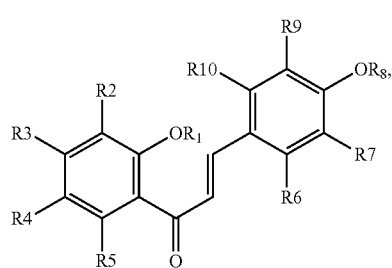

wherein R1 is hydrogen (H), each of R2 to R5 is H, hydroxide (—OH) or halogen (X), each of R6, R7, R9 and R10 is H, —OH, C$_1$ to C$_{20}$ alkoxy group or benzyloxy group, and R8 is H, C$_1$ to C$_{20}$ alkyl group and benzyl group.

Preferably, the composition is effective in regulating a pathway by inhibiting p44/42 MAPK phosphorylation or activating PPARγ, in which p44/42 MAPK phosphorylation is effective in promoting an expression of IL-6 and/or IL-1β, and PPARγ is effective in inhibiting an expression of IL-6 and/or IL-1β and effective in inhibiting an expression of cyclin D1 and/or cyclin D3.

The present invention further provides a composition for increasing a reproduction of PPARγ, including a chalcone compound (Formula I), which has the substituted groups as above.

Preferably, PPARγ is translated from a messenger RNA, and the composition is effective in increasing PPARγ expression.

The present invention further provides a pharmaceutical composition for inhibiting the cell proliferation of HASMCs and/or its inflammation, including a chalcone compound (Formula I, with the same substituted groups as above) and a ligand of PPARγ.

The present invention further provides a pharmaceutical composition inhibiting an inflammation, including an effective amount of a chalcone compound represented by formula II and an effective amount of (RS)-5-[4-(2-[methyl(pyridin-2-yl)amino]ethoxy)benzyl]thiazolidine-2,4-dione (rosiglitazone):

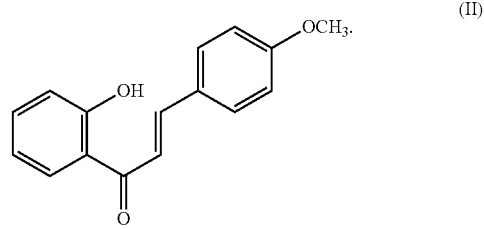 [SMILES: COc1ccc(/C=C/C(=O)c2ccccc2O)cc1]

Preferably, inflammation is a symptom of atherosclerosis.

The present invention further provides a pharmaceutical composition inhibiting the proliferation of smooth muscle cells, including an effective amount of a chalcone compound (Formula II) and an effective amount of 2-(2-amino-3-methoxyphenyl)-chromen-4-one (PD98059).

The above objectives and advantages of the present invention will become more readily apparent to those ordinarily skilled in the art after reviewing the following detailed descriptions and accompanying drawings.

DETAILED DESCRIPTION OF THE PREFERRED EMBODIMENT

Figure 1:
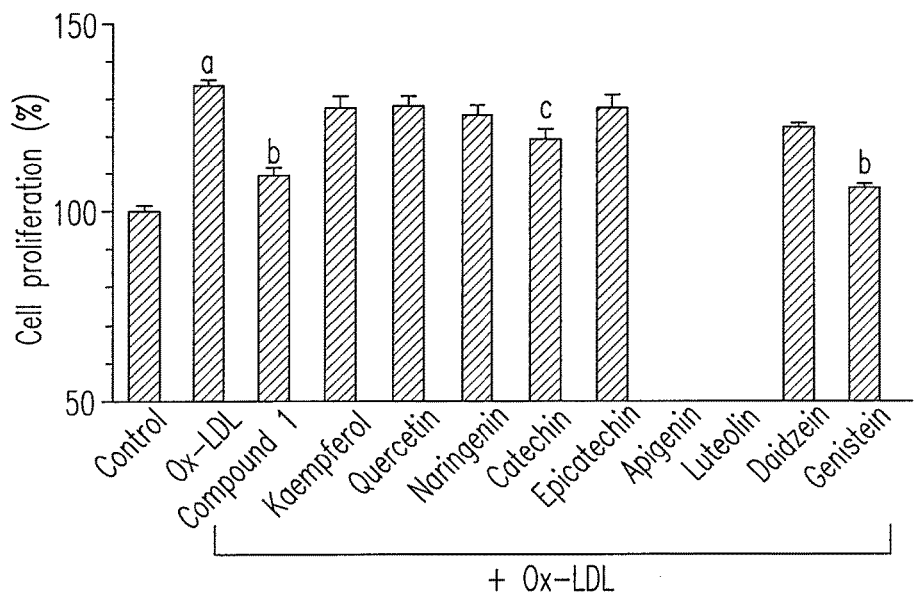
FIG. 1 is a diagram showing that the various flavonoid compounds (5 μg/ml) inhibit HASMCs proliferation induced by Ox-LDL (30 μg/ml) for 24 hours. Control is referred to a group that neither drug nor compound is added in cell culture medium. Data are represented as mean±standard deviation (S.D.) in six independent experiments. a: p<0.001 compared with control, b: p<0.001 compared with Ox-LDL-treated group, and c: p<0.01 compared with Ox-LDL-treated group.

The present invention will now be described more specifically with reference to the following Embodiments. It is to be noted that the following descriptions of preferred Embodiments of this invention are presented herein for purpose of illustration and description only; it is not intended to be exhaustive or to be limited to the precise form disclosed.

Embodiments

Experiment 1: Preparation of Chalcone Compounds

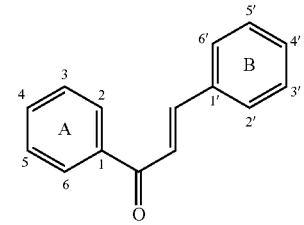

Chalcone compound has ring A and ring B. For ease of illustration, the denotations of carbon atoms on ring A and ring B are shown as above.

The synthesis of the chalcone compounds in the present invention was carried out by a Claisen-Schmidt condensation. Taking chalcone compound 1 as the example, a mixture of 2-hydroxyacetophenone (273.6 mg, 2.01 mmol), 4-methoxybenzaldehyde (279.1 mg, 2.05 mmol), potassium hydroxide (KOH, 50% w/v, 2 ml) and ethanol (100% v/v, 20 ml) was stirred at room temperature for 24 hours. The reaction mixture was concentrated under reduced pressure and then partitioned with ethyl acetate (EtOAc) and $H_2O$. The organic layer was then evaporated, and the residue was purified using column chromatography (silica gel: 70-230, Merck; n-hexane-EtOAc, 15:1, Rf=0.2) to give 2-hydroxy-4'-methoxychalcone (chalcone compound 1, 273.6 mg; yield, 53.6%). The purity of compound 1 was greater than 95%, which was determined by high-performance liquid chromatography (HPLC).

Chalcone compounds 1 to 29 of the present invention prepared based on the aforementioned prepared method are listed as follows. However, chalcone compounds are not limited in the examples of compounds 1 to 29, other chalcone compounds prepared by this method and spirit belong to the examples and the protecting scope of the present invention.

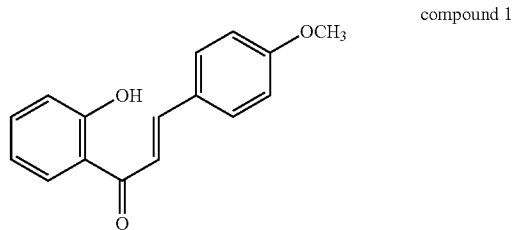

compound 1 compound 2 compound 3 compound 4 compound 5 compound 6 compound 7 compound 8 compound 9 compound 10 compound 11 compound 12 compound 13 compound 14 compound 15 compound 16
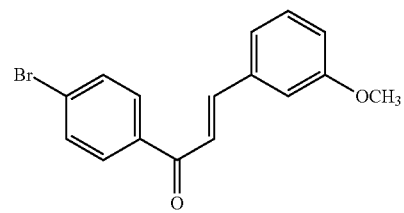
compound 17
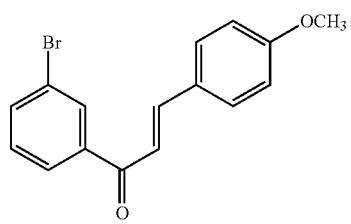
compound 18
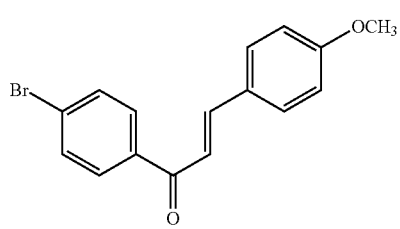
compound 19
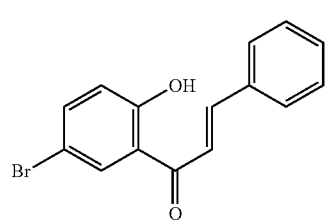
compound 20
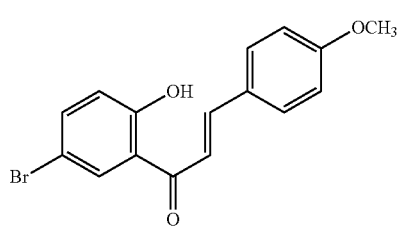
compound 21
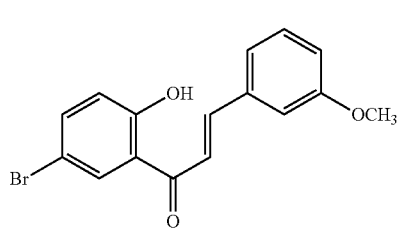
compound 22
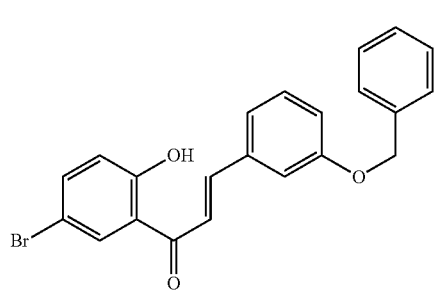
compound 23
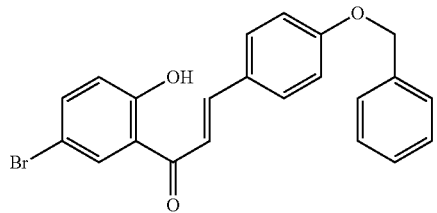
compound 24
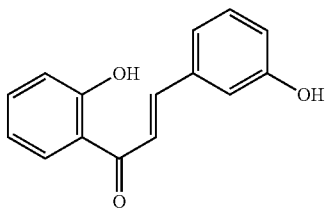
compound 25
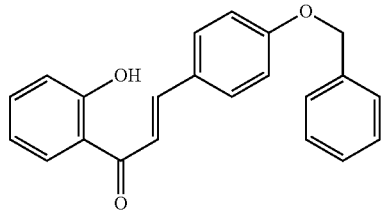
compound 26
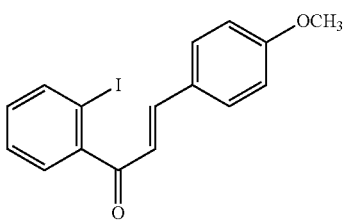
compound 27
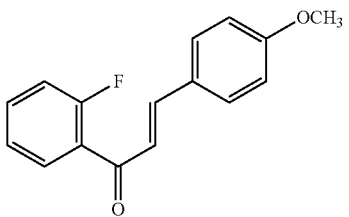
compound 28
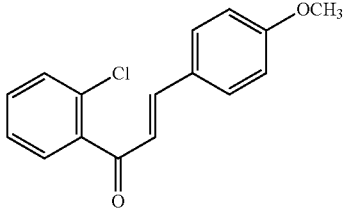
compound 29
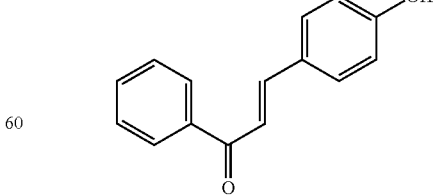
Experiment 2: Activity of Chalcone Compound 1 and Other Flavonoid Compounds on Inhibiting HASMCs Proliferation The skeleton of flavonoid compound is constructed by C6-C3-C6, and chalcone also belongs to this genus of structure. Generally speaking, the representative active flavonoid can be divided as six groups, including flavonol, flavanone, flavan-3-ol, flavone, isoflavone and anthocyanin. Followings are the basic skeleton in each genus of flavonoid compounds and the examples used in the present invention.

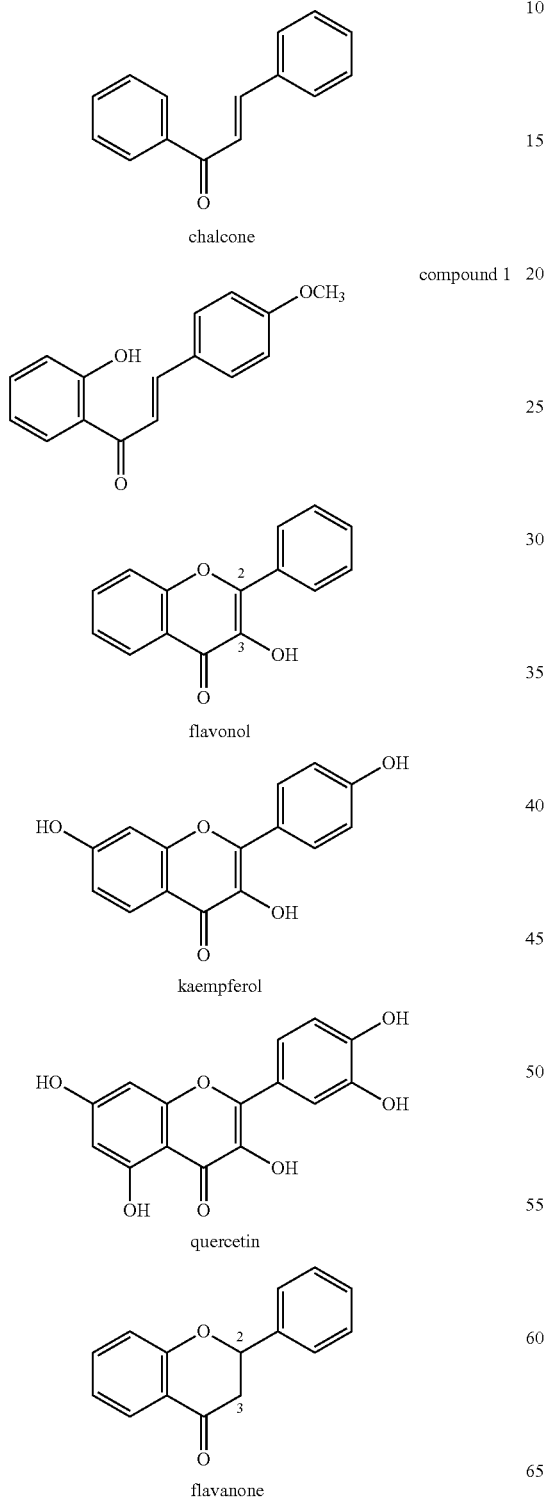

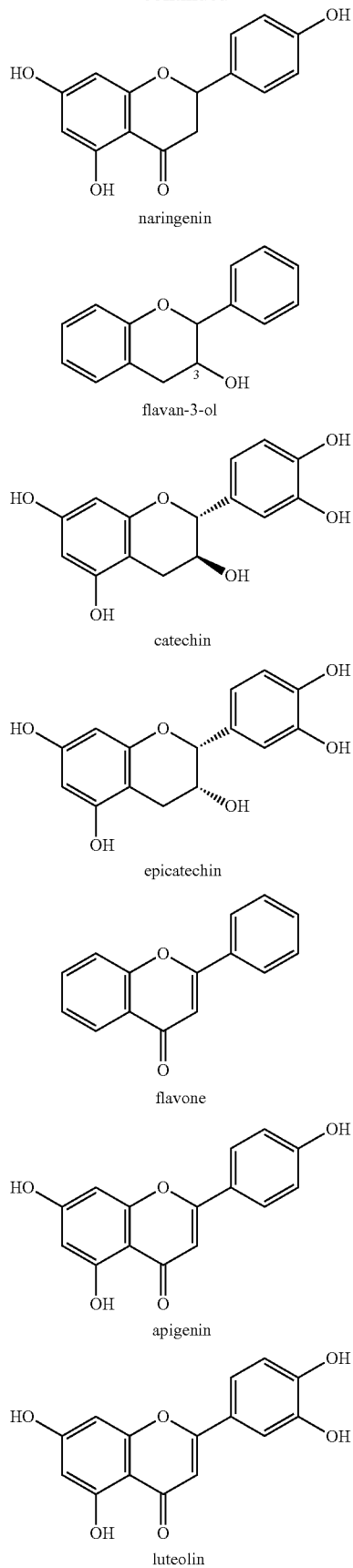

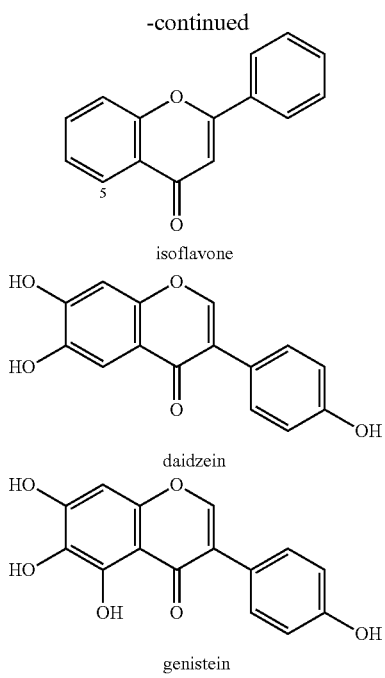

isoflavone daidzein genistein

For analyzing whether each genus of flavonoid compounds could inhibit the activity of HASMCs proliferation, the proliferation and cell viability of HASMCs were determined using WST-1 reagent (Roche Applied Science, Penzberg, Germany). WST-1 is a tetrazolium salt that will be cleaved to formazan by mitochondrial dehydrogenases in viable cells. First, HASMCs were seeded into 96-well plates. After the density reaching 70% confluence, the cells were "synchronized" for 24 hours by replacing the Dulbecco's Modified Eagle Medium (DMEM) as the flash DMEM supplemented with 0.5% fetal bovine serum (FBS). HASMCs were stimulated with 30 µg/ml Ox-LDL with or without the addition of flavonoid compound for 24 hours. At the end of incubation, WST-1 was added into cell medium and the amount of formazan was measured at a wavelength of 450 nm by an ELISA reader. The experimental method that proliferation and cell viability of HASMCs were determined using WST-1 would be performed in the present invention, and the same experimental procedures would not be repeatedly illustrated in the followings.

Please refer to FIG. 1, which is diagram showing that the various flavonoid compounds (5 µg/ml) inhibit the activity of HASMCs proliferation induced by Ox-LDL (30 µg/ml) for 24 hours. Incorporating the structural formulas of the aforementioned flavonoid compounds, compound 1, catechin and genistein had significant inhibition activity and were non-toxic to cells. Kaempferol, quercetin, naringenin and epicatechin didn't have significant inhibition activity, and apigenin and luteolin would lead to death of HASMCs. Comparing chalcone compound with flavonol and flavanone compounds, it could be known that only compound 1 had inhibition activity, whereas kaempferol and quercetin which were the species of flavonol, and naringenin which was the species in flavanone didn't have inhibition activity. The presence or absence of the double bond (C-2 to C-3) between flavonol and flavanone compounds was not the key factor for affecting activity. Chalcone compounds had inhibition activity until flavonol and flavanone compounds were ring-opened as chalcone compounds. Compound 1 and catechin had the similar inhibition activity, while compound 1 was slightly better than catechin. Additionally, the structural difference between catechin and epicatechin was that the stereo-configuration of hydroxyl at C-3 position, whereas the inhibition activity of catechin was better than that of epicatechin, indicating that C-3 stereo configuration of flavan-3-ol compounds was relevant to inhibition activity. Upon the comparison of compound 1 with isoflavone compounds, the inhibition activity of genistein was closed to that of compound 1 but was higher than that of diadzein. Since the structural difference between diadzein and genistein lied in the presence or absence of hydroxy at C-5 position, isoflavone compounds' activities were relevant to C-5 substituent.

Since compound 1 had inhibition activity on HASMCs proliferation and was non-toxic to cells, as compared with other five types of flavonoid compounds, chalcone compound 1 was selected to perform the following experiments.

Figure 2:
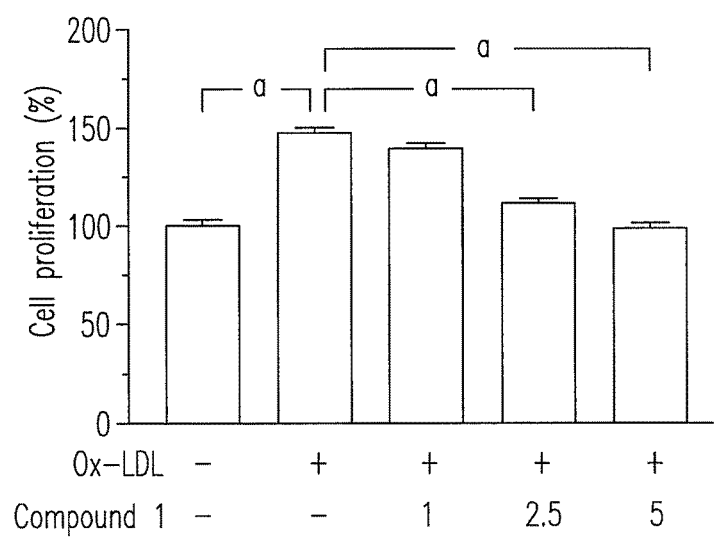
FIG. 2 is a diagram showing the inhibition effect of compound 1 (1, 2.5 and 5 μg/ml) on HASMCs proliferation induced by Ox-LDL (30 μg/ml) for 24 hours. Data are represented as mean±S.D. in six independent experiments. a: p<0.001.

Experiment 3: Anti-Proliferation Effect of Compound 1 on HASMCs Stimulated with Ox-LDL Please refer to FIG. 2, Ox-LDL (30 µg/ml) increased cell proliferation about 50% in HASMCs. As compared to Ox-LDL treatment group, cell proliferation of compound 1 treatment (1, 2.5 and 5 µg/ml) significantly decreased in a dose dependent manner.

Experiment 4: Mechanisms of Chalcone Compounds on Preventing and Treating Atherosclerosis 1. the Inhibition Activity of Compound 1 is Via p42/42 MAPK Phosphorylation For analyzing the mechanisms of compound 1 on inhibiting HASMCs proliferation, the cellular marker for proliferation, Ki-67 protein (also known as MKI67), detected with green fluorescence was the index for HASMCs proliferation. The experiment method was to stimulate HASMCs with Ox-LDL (30 µg/ml) for 24 hours, and simultaneously compound 1 (5 µg/ml) or PD98059 (an ERK 1/2 inhibitor, $10^{-5}$ M) was added. A mouse anti-Ki-67 monoclonal antibody was combined with a DyLight™488-conjugated second antibody to confirm the HASMCs proliferation. DAPI (4', 6-diamidino-2-phenylindole), a fluorescent stain that binds strongly to DNA, was used to localize cell nuclei. Cells were observed under flourescence microscopy. The proliferative cells were quantified by counting the ratio of DyLight™488 (green) fluorescence and DAPI (blue) fluorescence.

Figure 3:
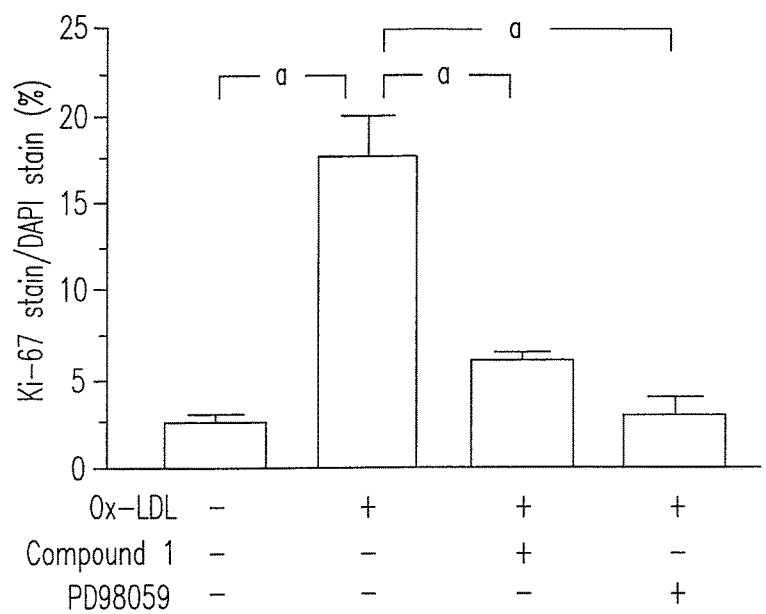
FIG. 3 is a diagram showing the effects of compound 1 and PD98059 on Ki-67 protein expression. HASMCs were treated with Ox-LDL (30 µg/ml) and either compound 1 (5 µg/ml) or PD98059 ($10^{-5}$ M) for 24 hours. Data are represented as mean±S.D. in three independent experiments. a: $p<0.001$.

Ox-LDL significantly increased the positive stains of Ki-67 protein in HASMCs, whereas the administration of compound 1 or PD98059 decreased the positive stains of Ki-67. These results confirm that compound 1 and PD98059 could inhibit Ox-LDL induced HASMCs proliferation (data not shown). Please refer to FIG. 3, the Ki-67 positive cells were quantified and converted to a percentage. The result shows that compound 1 could reduce about 10% of proliferative cells compared to Ox-LDL stimulated HASMCs without administration of compound 1.

Figure 4:
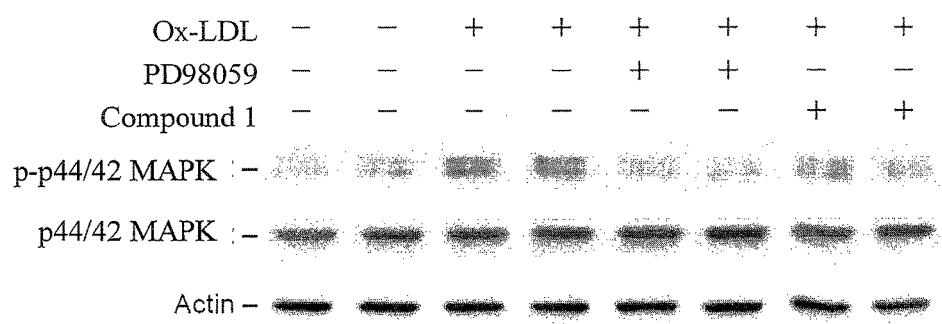
FIG. 4 is an immunoblotting spectrum showing the effects of compound 1 or PD98059 on p44/42 MAPK phosphorylation and total p44/42 MAPK expressions. HASMCs were treated with Ox-LDL (30 µg/ml) and either compound 1 (5 µg/ml) or PD98059 ($10^{-5}$ M) for 15 minutes. Two independent experiments are made in each group.

Please refer to FIG. 4, Ox-LDL increased p44/42 MAPK phosphorylation. In contrast, compound 1 demonstrated the similar effect of PD98059 to inhibit p44/42 MAPK phosphorylation, indicating that the anti-proliferation effects of compound 1 was mediated by p44/42 MAPK signaling.

2. Effects of Compound 1 on IL-1β and IL-6 Expressions

The anti-inflammatory effect of compound 1 was determined by the mRNA expressions of IL-1β and IL-6. HASMCs were stimulated with Ox-LDL (30 µg/ml) for 8 hours, and simultaneously treated with (i) PD98059 (5 µg/ml), (ii) rosiglitazone (5 µg/ml), (iii) compound 1 (5 µg/ml) and (iv) rosiglitazone (5 µg/ml) plus compound 1 (5 µg/ml). Total RNA of HASMCs was extracted using Trizol reagent (Invitrogen) and quantified using the Quant-iT™

RNA assay kit (Invitrogen). For each sample, 2 μg of total RNA were used to synthesize complementary DNA (cDNA) using the SuperScript™ III reverse transcriptase kit (Invitrogen). The cDNA was then diluted with water at a ratio of 1:9, and aliquots were amplified using the iQ™ SYBR Green Supermix (Bio-Rad Laboratories, Hercules, USA). cDNA and primers were added to the PCR mixture to a final volume of 20 μl. The PCR reaction was performed using the MiniOpticon real-time PCR system (Bio-Rad Laboratories, Hercules, USA). SEQ ID Nos: 1 and 2 were paired in amplification of IL-1β gene, SEQ ID Nos: 3 and 4 were paired in amplification of IL-6 gene, SEQ ID Nos: 5 and 6 were paired in amplification of PPARα gene, SEQ ID Nos: 7 and 8 were paired in amplification of PPARγ gene, and SEQ ID Nos: 9 and 10 were paired in amplification of β-actin gene.

Figure 5A:
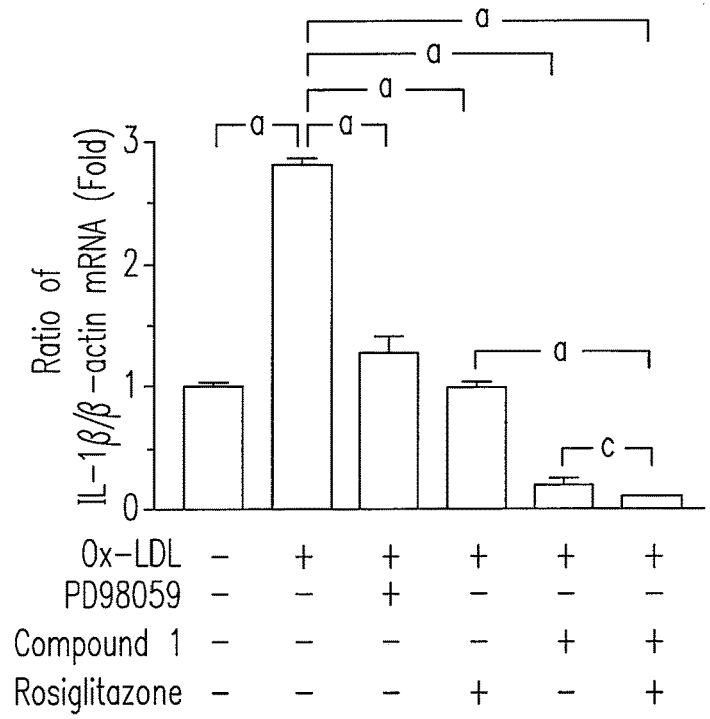
FIG. 5(a) and FIG. 5(b) are the effects of PD98059, compound 1 and/or rosiglitazone on (a) IL-1β mRNA expression and (b) IL-6 mRNA expression. HASMCs are treated with Ox-LDL (30 µg/ml), as well as PD98059 ($10^{-5}$ M), compound 1 (5 µg/ml), rosiglitazone (5 µg/ml) or compound 1 (5 µg/ml) plus rosiglitazone (5 µg/ml) for 24 hours. Data are represented as mean±S.D. in three independent experiments. a: $p<0.001$, c: $p<0.05$.
Figure 5B:
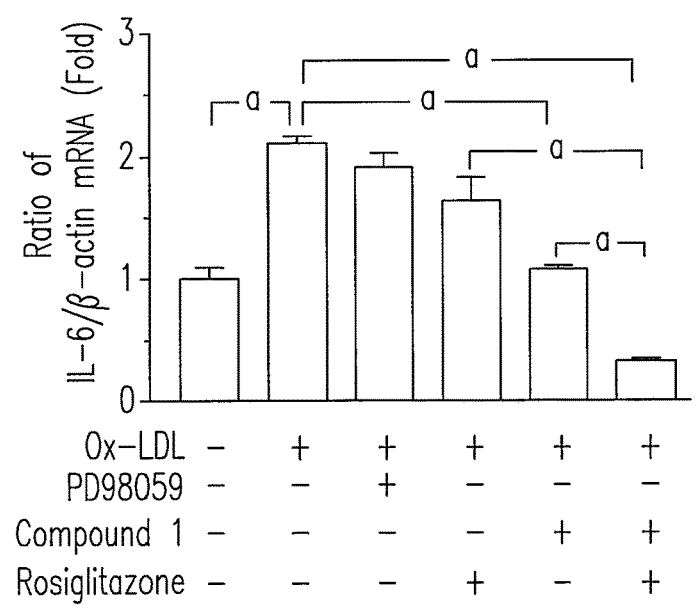

Please refer to FIGS. 5(a) and 5(b), Ox-LDL stimulated IL-1β and IL-6 mRNA overexpression in HASMCs, whereas administration of compound 1 significantly reversed the Ox-LDL effect on both IL-1β and IL-6 mRNA expression. PD98059 and rosiglitazone (an PPARγ agonist) only inhibited IL-1β mRNA expression but not IL-6 mRNA expression in HASMCs induced by Ox-LDL. The inhibition effect of compound 1 was better than that of rosiglitazone. The administration of rosiglitazone combined with compound 1 had the better activity in inhibiting IL-1β and IL-6 mRNA expression than that of rosiglitazone alone or compound 1 alone. In addition, in accordance with the protein analysis results from six independent experiments in FIGS. 5(a) and 5(b), it showed that IL-1β and IL-6 protein expression was consistent with their mRNA expression (data not shown). These results showed that chalcone compound could synergistically activate PPARγ related signaling transmission pathway with rosiglitazone.

3. Effects of Compound 1 on PPARγ Expression

Figure 6A:
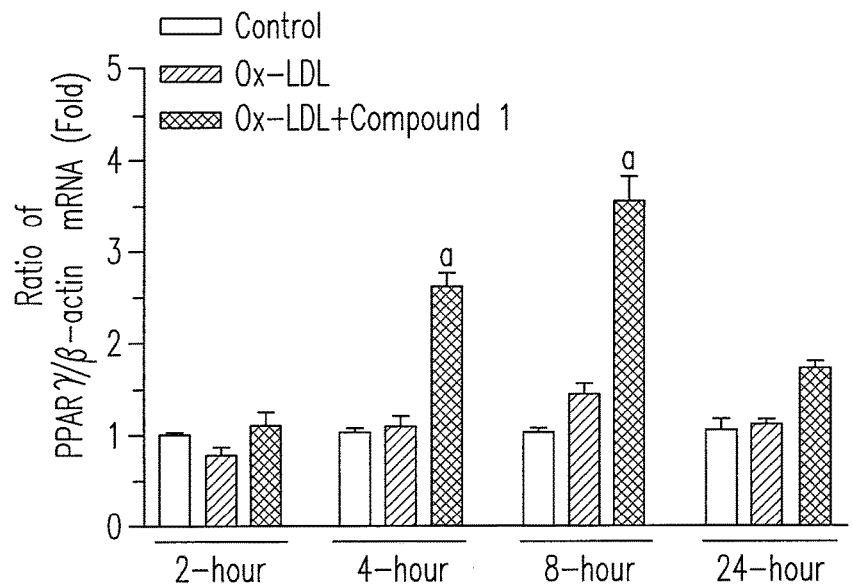
FIG. 6(a) and FIG. 6(b) are the effects of Ox-LDL and/or compound 1 on (a) PPARγ mRNA expression and (b) PPARα mRNA expression. HASMCs are treated with either Ox-LDL (30 µg/ml) alone or the combination of Ox-LDL (30 µg/ml) and compound 1 (5 µg/ml) respectively for 2, 4, 8 and 24 hours. Data are represented as mean±S.D. in three independent experiments. a: $p<0.001$ compared with Ox-LDL-treated group.
Figure 6B:
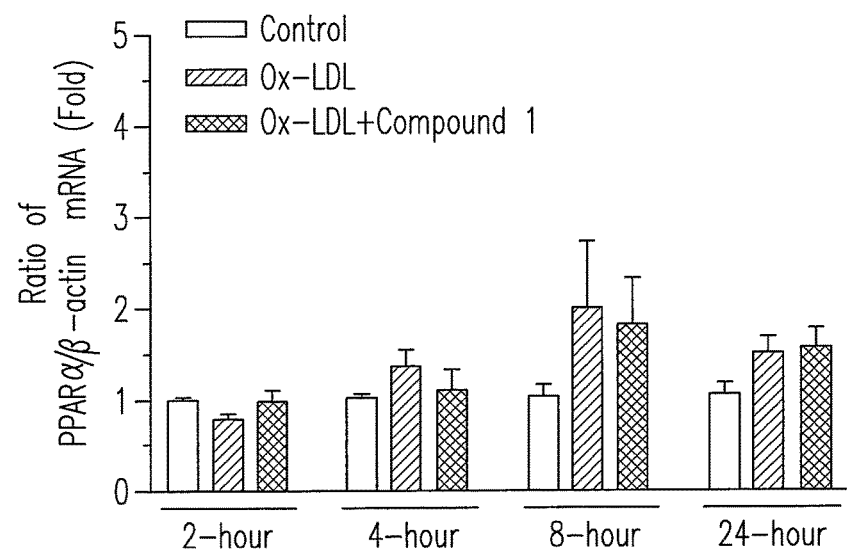

This experiment was performed to investigate the regulatory mechanism of compound 1 on PPARγ based on PPARγ mRNA expression in HASMCs. HASMCs were stimulated with Ox-LDL (30 μg/ml) with or without the addition of compound 1 (5 μg/ml) at the same time for 2, 4, 8 and 24 hours. Please refer to FIG. 6(a), Ox-LDL did not stimulate PPARγ mRNA expression, but compound 1 significantly increased PPARγ mRNA expression post 4 hours administration and a maximum was reached after 8 hours. Please refer to FIG. 6(b), neither Ox-LDL nor compound 1 stimulated PPARα mRNA upregulation, indicating that compound 1 may only activate PPARγ related signaling transmission pathway.

Figure 7A:
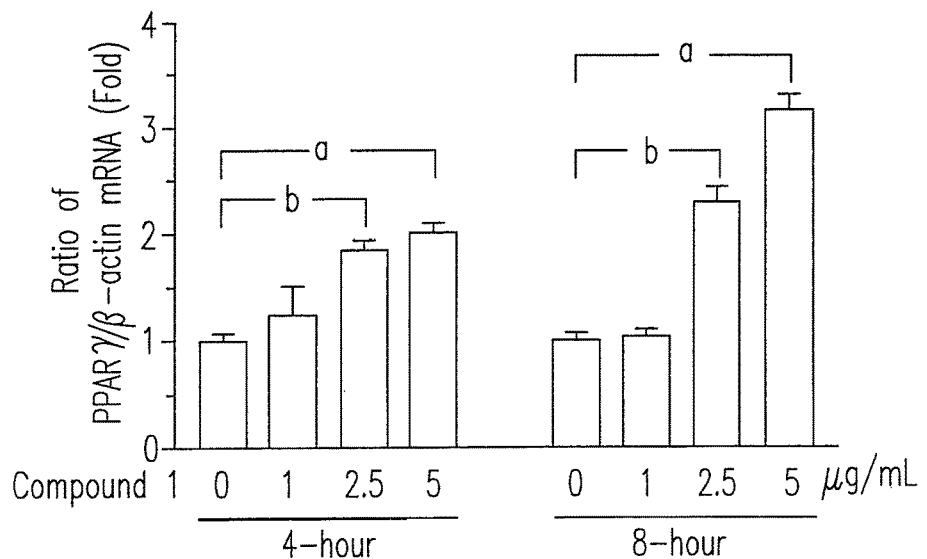
FIG. 7(a) and FIG. 7(b) respectively are (a) the diagram showing PPARγ mRNA expression and (b) an immunoblotting spectrum showing the PPARγ protein expression of compound 1 (0, 1, 2.5 and 5 µg/ml) on HASMCs for 4 and 8 hours. Data are represented as mean±S.D. in three independent experiments. a: $p<0.001$, b: $p<0.01$.
Figure 7B:
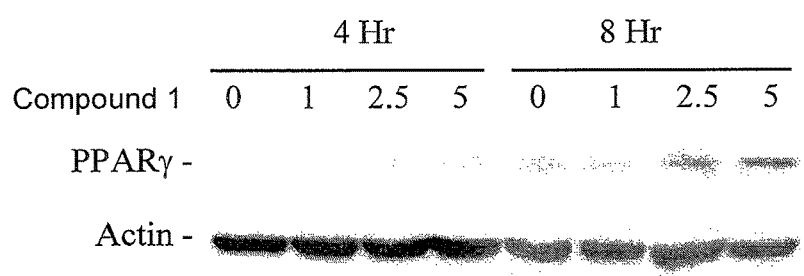

To further confirm whether compound 1 is an inducer of PPARγ for HASMCs, cells were stimulated with compound 1 alone. Please refer to the bar chart in FIG. 7(a) and the immunoblotting spectrum in FIG. 7(b), compound 1 significantly increased PPARγ mRNA and protein expression in dose and time dependent manners.

Figure 8A:
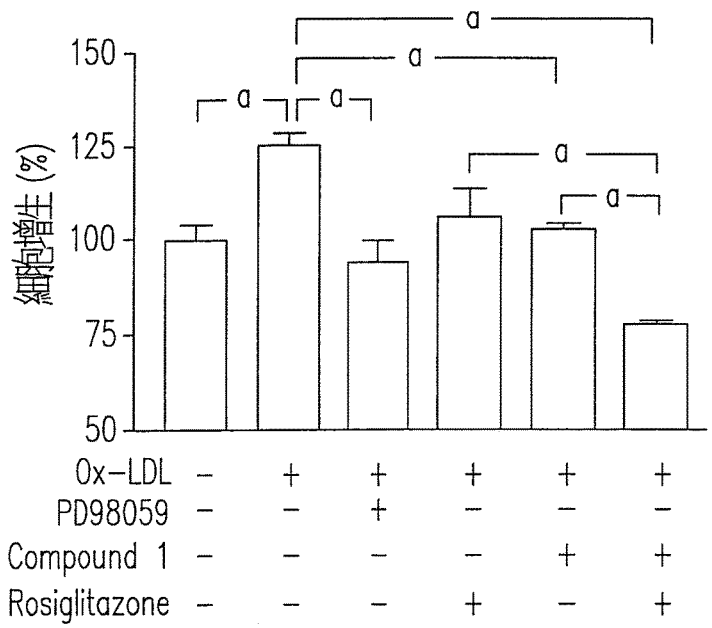
FIG. 8(a) is the diagram showing the effects of PD98059, compound 1 and/or rosiglitazone on HASMCs proliferation induced by Ox-LDL. HASMCs are treated with Ox-LDL (30 µg/ml), as well as PD98059 ($10^{-5}$ M), compound 1 (5 µg/ml), rosiglitazone (5 µg/ml) or the combination of compound 1 (5 µg/ml) and rosiglitazone (5 µg/ml) for 24 hours. Data are represented as mean±S.D. in six independent experiments. a: $p<0.001$.
Figure 8B:
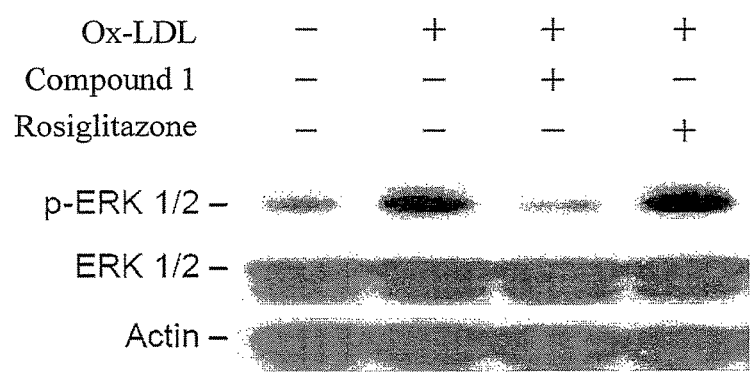
FIG. 8(b) is an immunoblotting spectrum showing the effects of PD98059, compound 1 and/or rosiglitazone on p44/42 MAPK phosphorylation and total p44/42 MAPK expressions of HASMCs induced by Ox-LDL. HASMCs are treated with Ox-LDL (30 µg/ml), as well as compound 1 (5 µg/ml) or rosiglitazone (5 µg/ml) for 15 minutes. Three independent experiments are made in each group.

4. Compound 1 Synergistically Works with PPARγ Agonist to Inhibit Proliferation in HASMCs Please refer to FIG. 8(a), administration of PD98059 or compound 1 alone significantly inhibited HASMCs proliferation induced by Ox-LDL, whereas administration of rosiglitazone alone did not significantly inhibit the HASMCs proliferation. In contrast, administration of rosiglitazone with compound 1 could decrease the proliferation lower than the control group about 20%, without the observation of cytotoxicity. This effect may result from the inhibition of p44/42 MAPK and activation of PPARγ at the same time. Please refer to the immunoblotting spectrum in FIG. 8(b), it demonstrated that compound 1 significantly inhibited p44/42 MAPK phosphorylation, whereas rosiglitazone did not.

Figure 9:
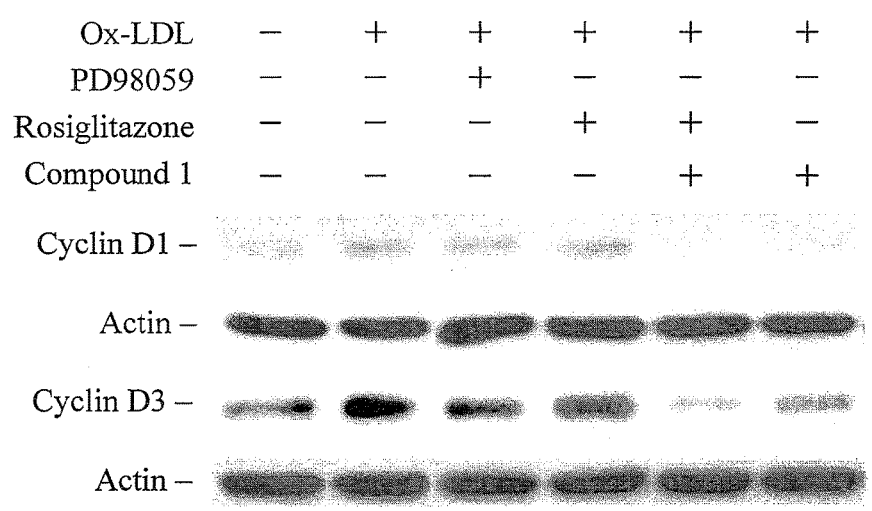
FIG. 9 is an immunoblotting spectrum showing the effect of Ox-LDL, as well as PD98059, rosiglitazone and/or compound 1 on cyclin D1 and cyclin D3 expressions. HASMCs were treated with Ox-LDL (30 µg/ml) alone, or PD98059 ($10^{-5}$ M), compound 1 (5 µg/ml), rosiglitazone (5 µg/ml) or the combination of compound 1 (5 µg/ml) and rosiglitazone (5 µg/ml) for 8 hours. Three independent experiments are made in each group.

5. Compound 1 Synergistically Works with PPARγ Agonist to Inhibit Cyclin D1 and D3 in HASMCs Please refer to FIG. 9, Ox-LDL increased cyclin D1 and D3 protein expression in HASMCs. The administration of PD98059 or rosiglitazone did not significantly decrease cyclin D1 and D3 protein expression. In contrast, compound 1 treatment significantly inhibited cyclin D1 and D3 protein upregulation induced by Ox-LDL. Moreover, treatment of compound 1 with rosiglitazone could further decrease cyclin D1 and D3 protein expression.

6. Summary

The abovementioned experimental results have been demonstrated that chalcone compound 1 had significant anti-proliferation and anti-inflammation effects in HASMCs. The mechanisms may mediate via the inhibition of p44/42 MAPK, cyclin D1 and D3, and the activation of PPARγ by compound 1. Compound 1 is a PPARγ inducer and a novel candidate for the treatment of atherosclerosis. Compound 1 can be further manufactured as the pharmaceutical composition or drugs with different dosage forms by the prior art in pharmacology.

Figure 10:
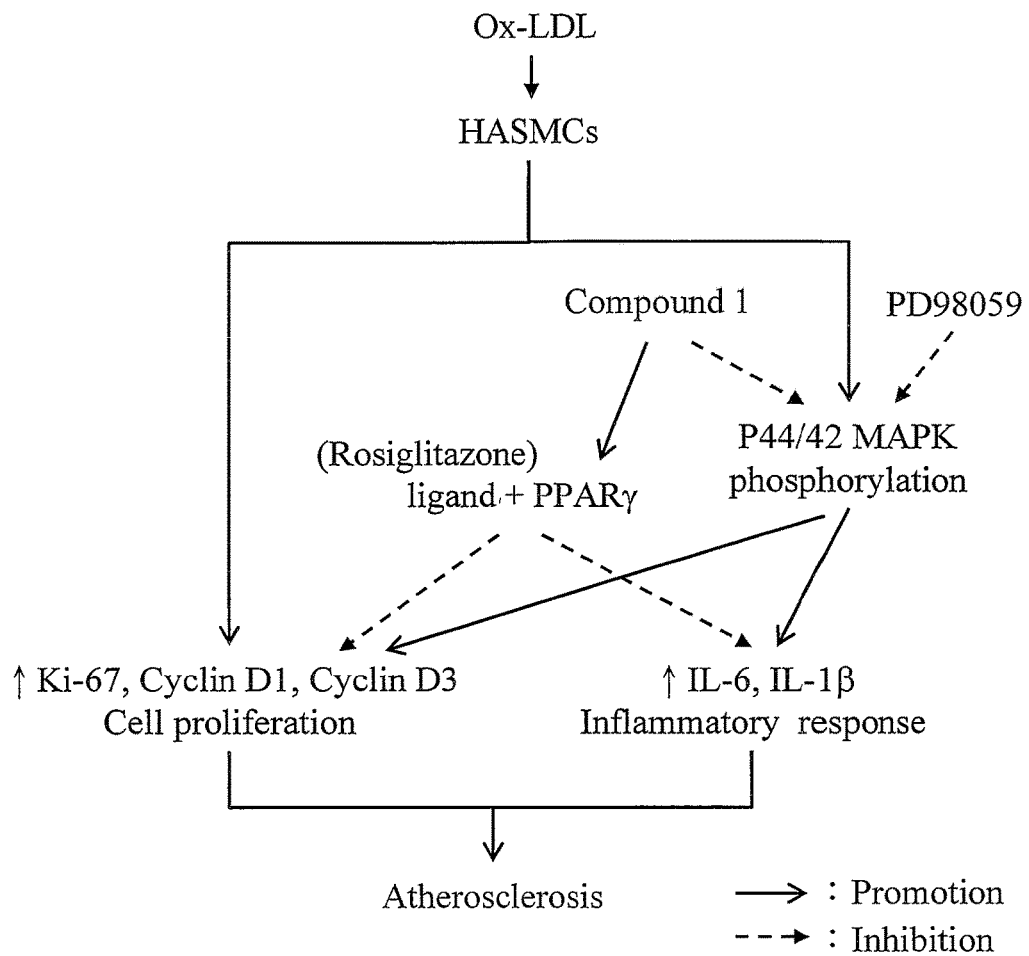
FIG. 10 is the diagram showing the anti-atherosclerosis mechanism of compound 1. Solid line is referred to promotion while dash line is referred to inhibition.

Please refer to FIG. 10, the abovementioned experimental results were shown as the signaling transmission pathway. Ox-LDL induced p44/42 MAPK phosphorylation in HASMCs. Compound 1 inhibited p44/42 MAPK phosphorylation induced by Ox-LDL, indicating that compound 1 inhibited HASMCs proliferation via the inactivation of p44/42 MAPK signaling transmission.

Ox-LDL stimulated the expression of inflammatory cytokines, IL-1β and IL-6, in HASMCs, and compound 1, PD98059 and rosiglitazone significantly inhibited IL-1β expression induced by Ox-LDL, indicating that IL-1β expression induced by Ox-LDL was regulated via p44/42 MAPK signaling transmission pathway, and the inhibition effect of compound 1 on IL-1β was regulated via this pathway. The inhibition effect of compound 1 was better than that of PD98059, indicating that compound 1 might regulate IL-1β expression via other pathways. Rosiglitazone (PPARγ ligand) achieved the anti-inflammatory activity by reducing IL-1β overexpression, whereas PD98059 or rosiglitazone cannot inhibit IL-6 expression induced by Ox-LDL. The treatment of compound 1 combined with rosiglitazone on HASMCs was able to decrease IL-6 expression, compared to treatment of compound 1 alone, indicating that compound 1 and rosiglitazone synergistically regulated IL-6 expression.

The administration of compound 1 increased mRNA expression mRNA expression of PPARγ, but not PPARα. Compound 1 is a PPARγ inducer to increase the endogenous PPARγ production for offering its ligand binding in HASMCs. HASMCs treated with rosiglitazone alone could not sufficiently inhibit the proliferation induced by Ox-LDL. In contrast, treatment that combined compound 1 with rosiglitazone demonstrated the best inhibition effect on HASMCs proliferation, compared to the treatment with PD98059, rosiglitazone or compound 1 alone, indicating that only administration of the ligand without its binding target was not sufficient to activate PPARγ related pathway in HASMCs. Rosiglitazone showed no effect on inhibiting p44/42 MAPK signaling, whereas compound 1 demonstrated the dual effects as p44/42 MAPK inhibitor and as PPARγ inducer offering binding target for rosiglitazone.

Therefore, treatment combined PPARγ ligand with PPARγ inducer such as compound 1 may be a novel therapeutic direction for atherosclerosis.

Cyclin D1 and D3 were upregulated by Ox-LDL which indicated that HASMCs proliferation may be mediated via cyclin D1 and D3. Compound 1, but not PD98059 and rosiglitazone, significantly decreased the cyclin D1 and D3 upregulation, implying that the inhibitory effect of compound 1 on cyclin D1 and D3 may be mediated through other mechanism. Simultaneous administration of compound 1 and rosiglitazone could further decrease cyclin D1 and D3 proteins, suggesting that PPARγ may still play partial role in controlling cell cycle regulators. The experimental results suggest that treatment combined PPARγ inducer (such as compound 1) and PPARγ ligand could efficiently reduce cyclin D1 and D3 production stimulated by Ox-LDL in HASMCs.

In conclusion, chalcone compound 1 can be used in treatment of atherosclerosis by regulating multiple signaling transmission pathways.

Experiment 5: Chalcone Compounds Inhibit the Activity of HASMCs Proliferation

Chalcone compounds 1 to 29 at different concentrations prepared in Experiment 1 were used to determine the effect of HASMCs proliferation induced by LPS. In Experiment 3, it was demonstrated that the various concentrations (1, 2.5 and 5 μg/mL) of compound 1 could significantly decrease cell proliferation. In reference to the drug concentration for cytotoxicity that HASMCs tolerate, the chalcone compounds having the relevant substituents to compound 1 were selected (rather than all chalcone compounds) to compare with each other at the same concentration.

Figure 11A:
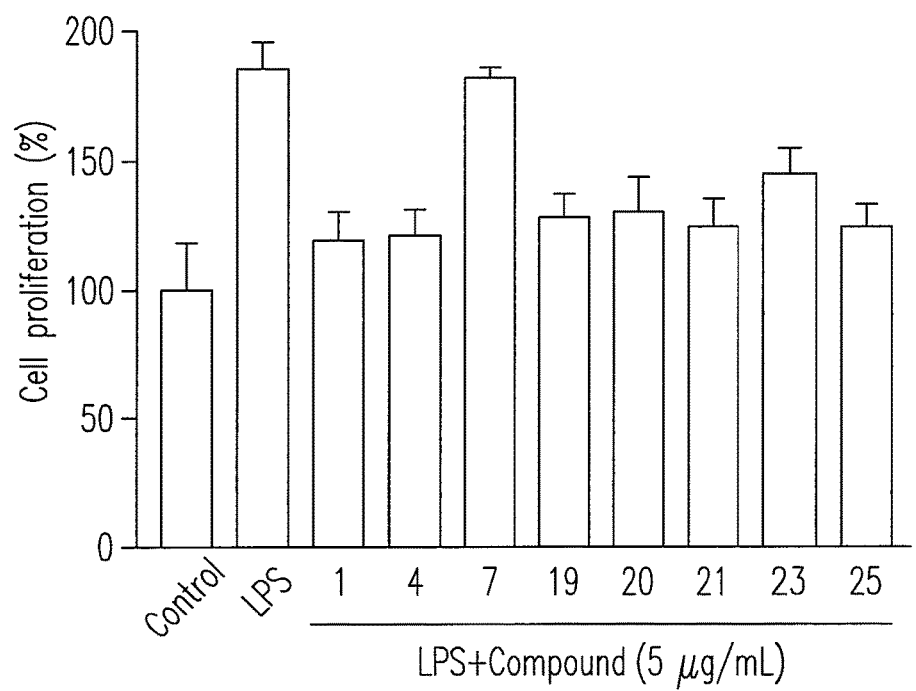
FIGS. 11(a), 11(b) and 11(c) respectively are the diagrams showing the effect of the various chalcone compounds of (a) 5 µg/ml, (b) 2.5 µg/ml and (c) 2 µg/ml on HASMCs proliferation induced by LPS. Control is referred to a group that neither drug nor compound is added in cell culture medium.

Please refer to FIG. 11(a), which is the diagram showing the effect of compounds 1, 4, 7, 19-21, 23 and 25 (5 μg/ml) on HASMCs proliferation induced by LPS. Comparing compound 1 (4'-methoxy in ring B) with compound 4 (3'-methoxy in ring B), both had the similar inhibition activity, indicating that para-methoxy or meta-methoxy in ring B would promote inhibition activity of chalcone compounds. Comparing compound 1 (ring A with 2-hydroxy) with compound 7 (ring A without 2-hydroxy), compound 1 rather than compound 7 has inhibition activity, indicating that para-hydroxy in ring A of chalcone compound had effect on inhibition activity. Comparing compounds 19, 20, 21 and 23, the substituents and their positions in ring A are the same, but the substituents in ring B are not the same. Compounds 19, 20, 21 and 23 had inhibition activity but would lead to death of a part of cells (data not shown). Since compound 1 has 2-hydroxy in ring A and has inhibition activity, compounds 19, 20, 21 and 23 (5 μg/ml) having 5-bromide in ring A would increase cytotoxicity. Comparing compound 1 with compound 21, compound 25 (5 μg/ml) would result in HASMC death, suggesting that its toxicity was originated from 4'-benzyloxy in ring B.

Figure 11B:
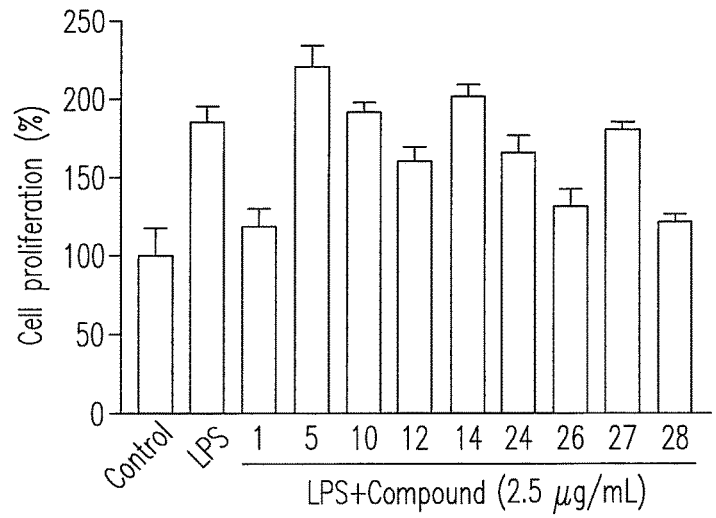

Please refer to FIG. 11(b), which is the diagram showing the effect of compounds 1, 5, 10, 12, 14, 24 and 26~28 (2.5 μg/ml) on HASMCs proliferation induced by LPS. Comparing compound 1 (ring A without 4-hydroxy) with compound 5 (ring A with 4-hydroxy), compound 1 rather than compound 5 had inhibition activity, indicating that 4-hydroxy in ring A would lead to the decrease of inhibition activity. Comparing compound 1 (ring B with 4'-methoxy) with compound 10 (ring B without 4'-methoxy), compound 10 did not have inhibition activity, indicating that 4'-methoxy in ring B of chalcone compound was the factor for inhibition activity. Comparing compound 1 (2-hydroxy in ring A) with compound 12 (2-bromide in ring A), compound 1 had better inhibition activity than compound 12, indicating that 2-hydroxy in ring A would result in better inhibition activity than 2-bromide in ring A. Comparing compound 12 (2-bromide in ring A and 4'-methoxy in ring B) and compound 14 (3-bromide in ring A and 3'-methoxy in ring B), compound 12 rather than compound 14 had inhibition activity, indicating that the respective positional attachments of bromide and methoxy in ring A and ring B would not result in compound's inhibition activity better than compound 1. Comparing compound 1 with compounds 12, 26, 27 and 28 (each having 2-halide in ring A), inhibition activity of compound 1 was better than those of compounds 12 and 27 and was slightly better than that of compounds 26 and 28.

Figure 11C:
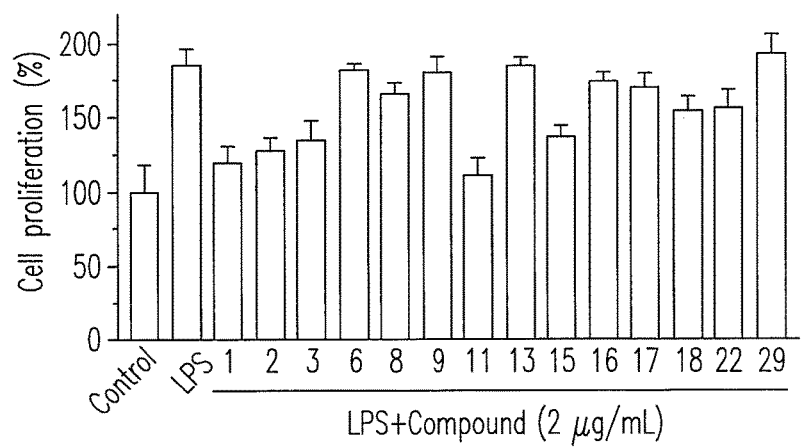

Please refer to FIG. 11(c), which is the diagram showing the effect of compounds 1~3, 6, 8~9, 11, 13, 15~18, 22 and 29 (2 μg/ml) on HASMCs proliferation induced by LPS. Compounds 2, 11, 15 and 22 would lead to death of a part cells (data not shown). Comparing compound 1 with compounds 2 and 3, compound 1 had better inhibition activity than compounds 2 and 3, indicating that 4-hydroxy in ring A of chalcone compounds had less effect in inhibition activity. Furthermore, comparing compounds 2 and 3, compound 2 showed toxicity at this dosage (2 μg/ml). Although compounds 2 and 3 had the same substituent in ring A, compound 3 had 4'-benzyloxy in ring B, suggesting that 4'-benzyloxy could reduce toxicity caused by 4-hydroxy in ring A. Comparing compound 3 (4'-benzyloxy in ring B) with compound 6 (3'-methoxy in ring B), compound 3 rather than compound 6 had inhibition activity, indicating that the specific 4'-substituent in ring B of chalcone compound could enhance its inhibition activity. Comparing compound 1 with compound 8, compound 8 that lacks particular substituent in ring A did not have inhibition activity, whereas compound 1 having 2-hydroxy in ring A did. Thus, the specific 2-substituent in ring A of chalcone compound showed the critical influence on inhibition activity. Furthermore, comparing compound 1 with compound 9, compound 9 showed no inhibition activity, indicating that the basic chalcone skeleton did not have inhibition activity. Comparing compound 1 with compound 11, 3'-benzyloxy in ring B of compound 1 would result in cytotoxicity enhancement. Comparing compound 1 with compounds 13, 15, 16, 17, 18 and 22 (ring A with hydroxyl or halide and ring B with methoxy or benzyloxy), compound 1 still had the best inhibition activity and was non-toxic to cells. Comparing compound 1 with compound 29, compound 29 had no inhibition activity, again showing that the specific 2-substituent in ring A of chalcone compound had the critical influence on inhibition activity.

The various chalcone compounds can be applied in Experiments 1 to 4 by one skilled in the art according to the aforementioned inhibition results. That is, each of chalcone compounds can be combined with PD98059 or rosiglitazone, to apply in treating or preventing atherosclerosis.

While the invention has been described in terms of what is presently considered to be the most practical and preferred Embodiments, it is to be understood that the invention needs not be limited to the disclosed Embodiments. On the contrary, it is intended to cover various modifications and similar arrangements included within the spirit and scope of the appended claims, which are to be accorded with the broadest interpretation so as to encompass all such modifications and similar structures.

What is claimed is:

1. A method to treat an atherosclerosis of a subject, comprising a step of:
administering to the subject in need thereof an effective amount of a chalcone compound represented by Formula I:

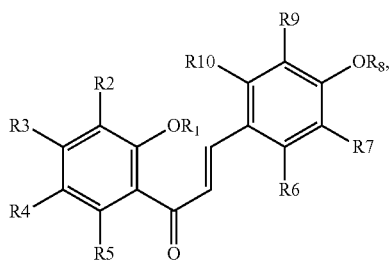

to treat the atherosclerosis,
wherein R1 is hydrogen, R3 is hydrogen, R4 is selected from hydrogen or halogen, each of R2, R5, R6, R7, R9 and R10 is hydrogen, and R8 is one of hydrogen and benzyl.

2. The method according to claim 1 being effective in regulating a pathway by one of inhibiting a p44/42 mitogen-activated protein kinase (MAPK) phosphorylation and activating a peroxisome proliferator activated receptor gamma (PPARγ).

3. The method according to claim 2, wherein the p44/42 MAPK phosphorylation is effective in promoting an expression of at least one of an interleukin-6 (IL-6) and an interleukin-1beta (IL-1β).

4. The method according to claim 2, wherein the PPARγ is effective in inhibiting an expression of at least one of an interleukin-6 (IL-6) and an interleukin-1beta (IL-1β).

5. The method according to claim 2, wherein the PPARγ is effective in inhibiting an expression of at least one of a cyclin D1 and a cyclin D3.

6. A method for increasing a reproduction of a peroxisome proliferator activated receptor gamma (PPARγ) in a subject, comprising a step of:
administering to the subject in need thereof an effective amount of a chalcone compound represented by Formula I:

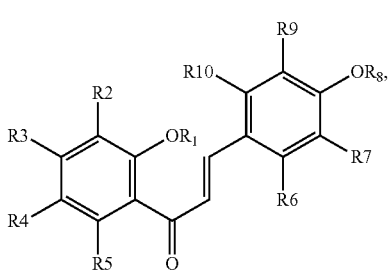

to increase the reproduction of the PPARγ,
wherein R1 is hydrogen, R3 is hydrogen, R4 is selected from hydrogen or halogen, each of R2, R5, R6, R7, R9 and R10 is hydrogen, and R8 is one of hydrogen and benzyl.

7. The method according to claim 6, wherein the PPARγ is translated from a messenger RNA, and the method is effective in increasing an expression of the messenger RNA.

* * * * *